(12) United States Patent
Zhao

(10) Patent No.: US 12,178,644 B2
(45) Date of Patent: Dec. 31, 2024

(54) DETACHMENT STRUCTURE FOR PORTABLE DIAGNOSTIC ULTRASOUND APPARATUS

(71) Applicant: Sonotecho Biomedical Co., Ltd, Guangdong (CN)

(72) Inventor: Xianyang Zhao, Guangdong (CN)

(73) Assignee: Sonotecho Biomedical Co., Ltd, Shenzhen (CN)

( * ) Notice: Subject to any disclaimer, the term of this patent is extended or adjusted under 35 U.S.C. 154(b) by 151 days.

(21) Appl. No.: 18/057,235

(22) Filed: Nov. 21, 2022

(65) Prior Publication Data

US 2024/0050065 A1 Feb. 15, 2024

(30) Foreign Application Priority Data

Aug. 11, 2022 (CN) .......................... 202222110212.8

(51) Int. Cl.
| | |
|---|---|
| *A61B 8/00* | (2006.01) |
| *H01M 10/46* | (2006.01) |
| *H01M 50/247* | (2021.01) |
| *H01M 50/262* | (2021.01) |
| *H01M 50/271* | (2021.01) |
| *H01M 50/284* | (2021.01) |
| *H02J 7/00* | (2006.01) |

(52) U.S. Cl.
CPC .......... *A61B 8/4411* (2013.01); *A61B 8/4427* (2013.01); *A61B 8/56* (2013.01); *H01M 10/46* (2013.01); *H01M 50/247* (2021.01); *H01M 50/262* (2021.01); *H01M 50/271* (2021.01); *H01M 50/284* (2021.01); *H01M 2220/30* (2013.01); *H02J 7/0042* (2013.01)

(58) Field of Classification Search
None
See application file for complete search history.

(56) References Cited

U.S. PATENT DOCUMENTS

| | | | | |
|---|---|---|---|---|
| 2008/0194963 | A1* | 8/2008 | Randall | A61B 8/00 600/459 |
| 2019/0336101 | A1* | 11/2019 | Chiang | A61B 1/00 |
| 2021/0137633 | A1* | 5/2021 | Mullani | G02B 25/008 |
| 2023/0225706 | A1* | 7/2023 | Rahardja | A61B 8/4472 600/437 |

* cited by examiner

*Primary Examiner* — Patricia J Park

(57) ABSTRACT

The present disclosure relates to the technical field of detachment structures, a detachment structure for a portable diagnostic ultrasound apparatus is disclosed, including: a top cover, a bottom housing, and a rechargeable battery, the top cover is detachably connected to the bottom housing, the bottom housing is installed with a fan, the bottom housing is installed with a battery PCB, the battery PCB is provided with a battery modular contact, and the top cover is provided with an opening for the battery modular contact to pass through. The solution facilitates detachable installation of the battery and the fan, and facilitates heat dissipation and maintenance.

9 Claims, 4 Drawing Sheets

DETACHMENT STRUCTURE FOR PORTABLE DIAGNOSTIC ULTRASOUND APPARATUS

CROSS REFERENCE TO RELATED APPLICATIONS

The present application claims the benefit of Chinese Patent Application No. 202222110212.8 filed on Aug. 11, 2022, the contents of which are incorporated herein by reference in their entirety.

FIELD

The present disclosure relates to the field of detachment structures, and more particularly, to a battery and fan detachment structure for a portable diagnostic ultrasound apparatus.

BACKGROUND

In the prior art, the portable diagnostic ultrasound apparatuses are mostly integrated and non-detachable. In addition, the battery will reach its life cycle (the capacity will decrease) after being used for about 1 to 1.5 years. The service time will be greatly shortened. If the battery needs to be replaced, it must be returned to the manufacturer for maintenance, which is inconvenient for users.

There are two ways to dissipate heat for the portable diagnostic ultrasound apparatus. One is to dissipate heat with a built-in fan. The disadvantages are: once the fan is damaged, it cannot dissipate heat normally, and the ultrasound apparatus cannot work normally, so it has to be returned to the manufacturer for maintenance. The other is to use a metal shell for heat dissipation, which can be subdivided into two types. One is that the shell is made of plastics, with parts of metal, the heat is dissipated through metal parts into air, and the heat dissipation effect is limited. The other is that the whole shell is made of metal. Although the heat dissipation effect is improved, the shell temperature is too high to be touched. If a thin shell of plastics or rubber is added outside the metal shell to reduce the temperature, the heat dissipation ability is also reduced. The more metal used, the heavier the ultrasound apparatus, and it's more inconvenient to use.

Therefore, how to provide a battery and fan detachment structure for a portable diagnostic ultrasound apparatus has become a technical problem to be solved.

SUMMARY

The technical problem to be solved by the present disclosure is how to provide a battery and fan detachment structure for a portable diagnostic ultrasound apparatus.

To this end, according to a first aspect, an embodiment of the present disclosure discloses a detachment structure for a portable diagnostic ultrasound apparatus, including: a top cover, a bottom housing, and a rechargeable battery installed between the top cover and the bottom housing, the top cover is detachably connected with the bottom housing, a fan is installed in the bottom housing, the fan is abutted with the top cover, a battery PCB is installed in the bottom housing, the battery PCB is provided with a battery modular contact, the top cover is provided with an opening for the battery modular contact to pass through.

The disclosure is further arranged that the bottom housing is provided with a slot for facilitating embedded installation of the top cover.

The disclosure is further arranged that the bottom housing is provided with an air outlet.

The disclosure is further arranged that the battery PCB is provided with a charging interface for charging the rechargeable battery.

The disclosure is further arranged that the charging interface is a TYPE-C interface.

The disclosure is further arranged that the bottom housing is provided with a undercut for facilitating clamping of the detachable structure.

The disclosure is further arranged that the circumference of the bottom housing is provided with a groove, and the top cover is provided with protrusions corresponding to the groove, and the groove is filled with waterproof glue therein.

According to a second aspect, an embodiment of the present disclosure discloses a portable diagnostic ultrasound apparatus, including: a main body front housing, a main body bottom housing, and the detachment structure for the portable diagnostic ultrasound apparatus according to the first aspect, the detachment structure being detachably connected within the main body bottom housing.

The disclosure is further arranged that the main body bottom housing is rotationally connected with a rotating switch for clamping the bottom housing, and the rotating switch is sleeved with a torsion spring.

The disclosure is further arranged that the main body bottom housing is provided with a toggle switch which is slidingly connected by a pressure spring for pressing the detachment structure, the pressure spring is installed inside the main body bottom housing for pressing the toggle switch.

The present disclosure has the following beneficial effects: since the rechargeable battery is arranged between the top cover and the bottom housing, the top cover is detachably connected with the bottom housing, the fan is installed in the bottom housing, and the battery modular contact is installed on the battery PCB, there is provided a detachment structure for the portable diagnostic ultrasound apparatus, thus facilitating detachable installation of the battery and the fan, and facilitating heat dissipation and maintenance.

BRIEF DESCRIPTION OF THE DRAWINGS

In order to more clearly explain the specific embodiments of the disclosure, the following will briefly introduce the drawings. Obviously, the drawings in the following description are some embodiments of the disclosure. For those of ordinary skills in the art, other drawings may also be obtained from these drawings.

Reference signs: 1. top cover; 11. opening; 2. bottom housing; 21. slot; 22. air outlet; 23. undercut; 24. groove; 25. installation slot; 3. rechargeable battery; 4. fan; 5. battery PCB; 6. battery modular contact; 7. charging interface; 8.

main body front housing; 9. main body bottom housing; 91. air inlet; 92. notch; 10. rotating switch; 11. toggle switch.

DETAILED DESCRIPTION OF THE EMBODIMENTS

In order to make the objectives, technical solutions and advantages of the disclosure more clear, the disclosure is further described in detail below in combination with the drawings and embodiments. It should be understood that the specific embodiments described herein are only used to explain the disclosure, not to define the disclosure.

In the description of the disclosure, it should be noted that, unless otherwise specified and defined, the terms "installation", "linking" and "connection" should be understood in a broad sense, for example, "connection" may be fixed connection, detachable connection, or integrated connection, may be mechanical connection or electrical connection, may be direct connection or indirect connection through an intermediate medium, may be internal connection of two elements, and may be USB cableless connection or USB cabled connection. For those of ordinary skills in the art, the specific meanings of the above terms in the present disclosure may be understood according to specific situations.

In the description of the disclosure, it should be noted that a directional or positional relationship indicated by terms such as "center", "top", "bottom", "left", "right", "vertical", "horizontal", "inside", "outside", etc. is based on a directional or positional relationship shown as the accompanying drawings and is merely intended to facilitate describing the present disclosure and simplifying the description, rather than to indicate or imply that the referred device or element has to be located in a specific direction or constructed and operated in the specific direction so as not to be understood as a restriction on the present disclosure. In addition, the terms "first", "second" and "third" are only used for describing purposes and cannot be understood as indicating or implying relative importance.

In addition, the technical features involved in different embodiments of the disclosure described below can be combined as long as there is no conflict between them.

Figure 1:
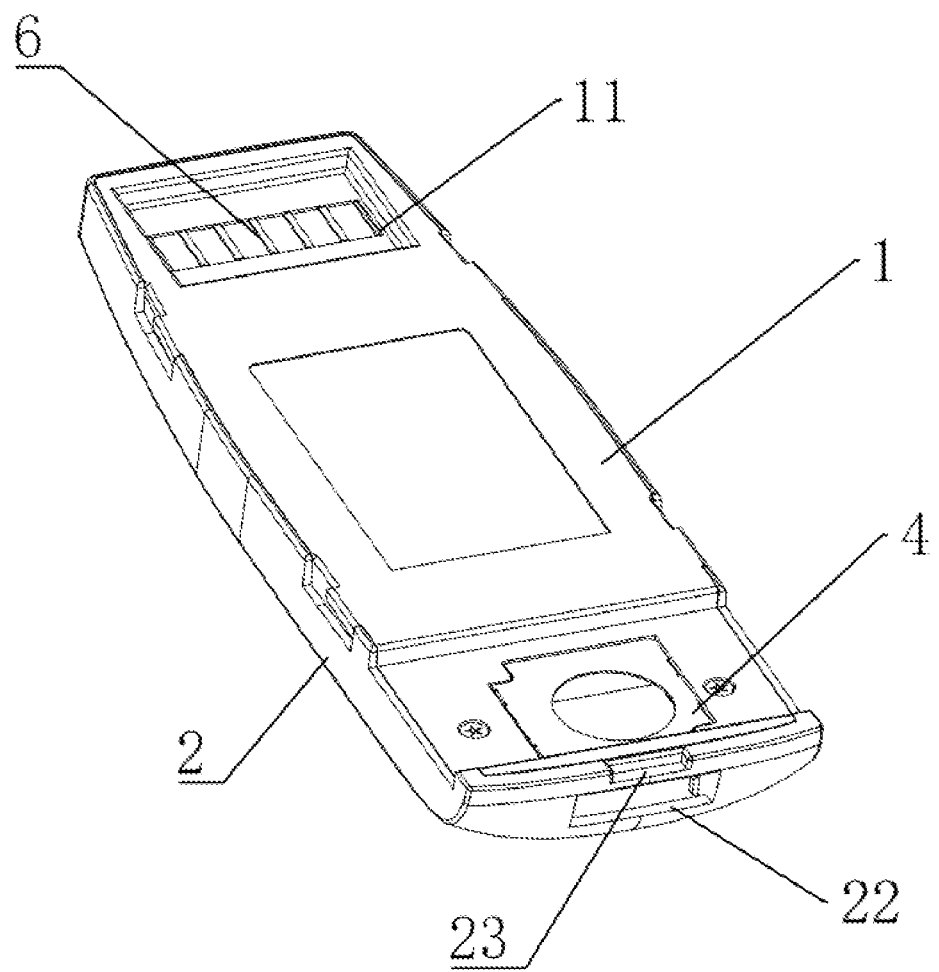
FIG. 1 is a structural diagram of a detachment structure for a portable diagnostic ultrasound apparatus disclosed in an embodiment.
Figure 2:
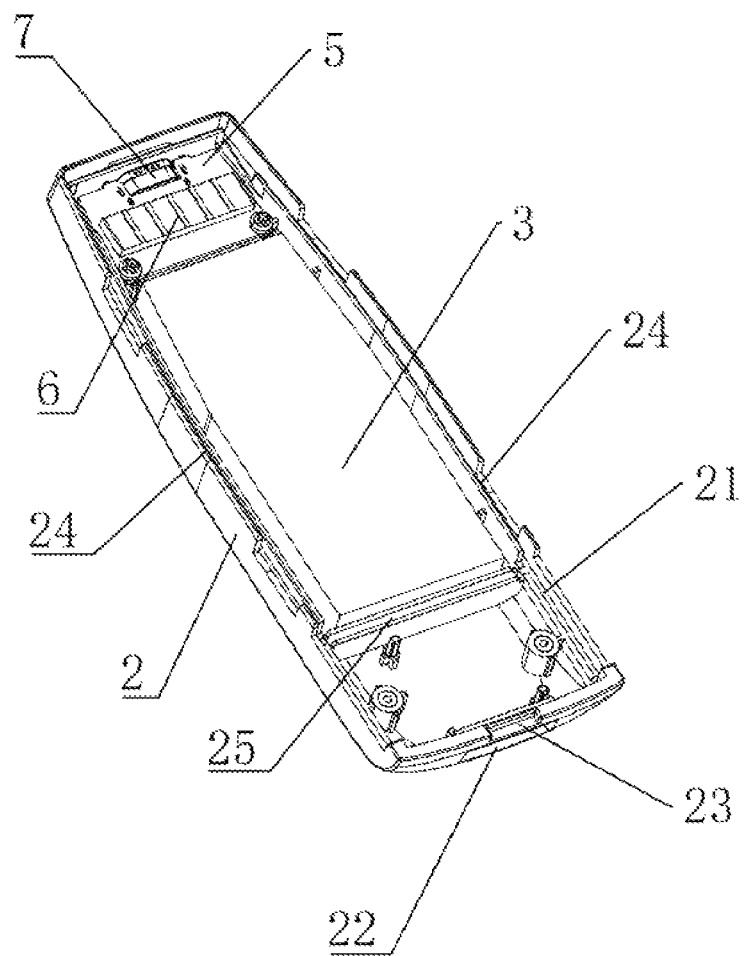
FIG. 2 is a structural diagram of a detachment structure for a portable diagnostic ultrasound apparatus disclosed in an embodiment.

The embodiment of the present disclosure discloses a detachment structure for a portable diagnostic ultrasound apparatus, as shown in FIG. 1 and FIG. 2, including: a top cover 1, a bottom housing 2, and a rechargeable battery 3 installed between the top cover 1 and the bottom housing 2, the top cover 1 is detachably connected with the bottom housing 2, a fan 4 is installed in the bottom housing 2, the fan 4 is abutted with the top cover 1, a battery PCB 5 is installed in the bottom housing 2, the battery PCB 5 is provided with a battery modular contact 6, the top cover 1 is provided with an opening 11 for the battery modular contact 6 to pass through.

It should be noted that since the rechargeable battery 3 is arranged between the top cover 1 and the bottom housing 2, the top cover 1 is detachably connected with the bottom housing 2, the fan 4 is installed in the bottom housing 2, the battery PCB 5 is provided with the battery modular contact 6, there is provided a detachment structure for the portable diagnostic ultrasound apparatus, thus facilitating detachable installation of the battery and the fan 4, and facilitating heat dissipation and maintenance.

As shown in FIG. 2, the bottom housing 2 is provided with a slot 21 for facilitating embedded installation of the top cover 1. It should be noted that the top cover 1 is embedded into the bottom housing 2 and fixed by screws so that the top cover 1 and the bottom housing 2 are reliably installed.

As shown in FIG. 2, the bottom housing 2 is provided with an air outlet 22. It should be noted that the air outlet 22 facilitates the dissipation of heat.

As shown in FIG. 2, the battery PCB 5 is provided with a charging interface 7 for charging the rechargeable battery 3. It should be noted that the charging interface 7 functions to facilitate charging of the rechargeable battery 3, charging requires only one USB cable, and does not require an additional charging holder, which is more convenient.

As shown in FIG. 2, the circumference of the bottom housing 2 is provided with a groove 24, and the top cover 1 is provided with protrusions corresponding to the groove 24, and the groove 24 is filled with waterproof glue therein, and the top cover 1 and the bottom housing 2 are fastened reliably, so that the IPX7 waterproof effect is achieved.

As shown in FIG. 2, a connector with a waterproof level of IPX8 is used in the charging interface 7, and the surface of the connector is provided with rubber, and the IPX7 waterproof effect can be achieved by interference fit of the circumference of the bottom housing 2 and the rubber of the connector.

As shown in FIG. 2, the circumference of the battery modular contact 6 is coated with waterproof glue, and after assembling the top cover 1, the gap between the top cover 1, the battery PCB 5, and the battery modular contact 6 is filled with the waterproof glue so as to reach the IPX7 waterproof effect.

As shown in FIG. 2, a waterproof fan is used for the fan 4, and an installation slot 25 is provided in the bottom housing 2 through which a cable for mounting the fan 4 passes. In the implementation, waterproof glue is applied inside the installation groove 25, the cable of the fan 4 is placed, and a layer of water glue is applied, so that the cable is completely wrapped with the waterproof glue, and finally the top cover 1 and the bottom housing 2 are fastened by snap-fitting, thereby achieving the IPX7 waterproof effect.

As shown in FIG. 2, the charging interface 7 is a TYPE-C interface. It should be noted that since the charging interface 7 is provided in the same type as the charging interface of the portable diagnostic ultrasound apparatus, only one charging USB cable is required for 2 pieces of battery in both the detachable structure and the main body of the portable diagnostic ultrasound apparatus, and there is no need for an additional charging holder, which is more convenient to use.

As shown in FIGS. 1 and 2, the bottom housing 2 is provided with an undercut 23 for facilitating clamping of the detachment structure.

Figure 3:
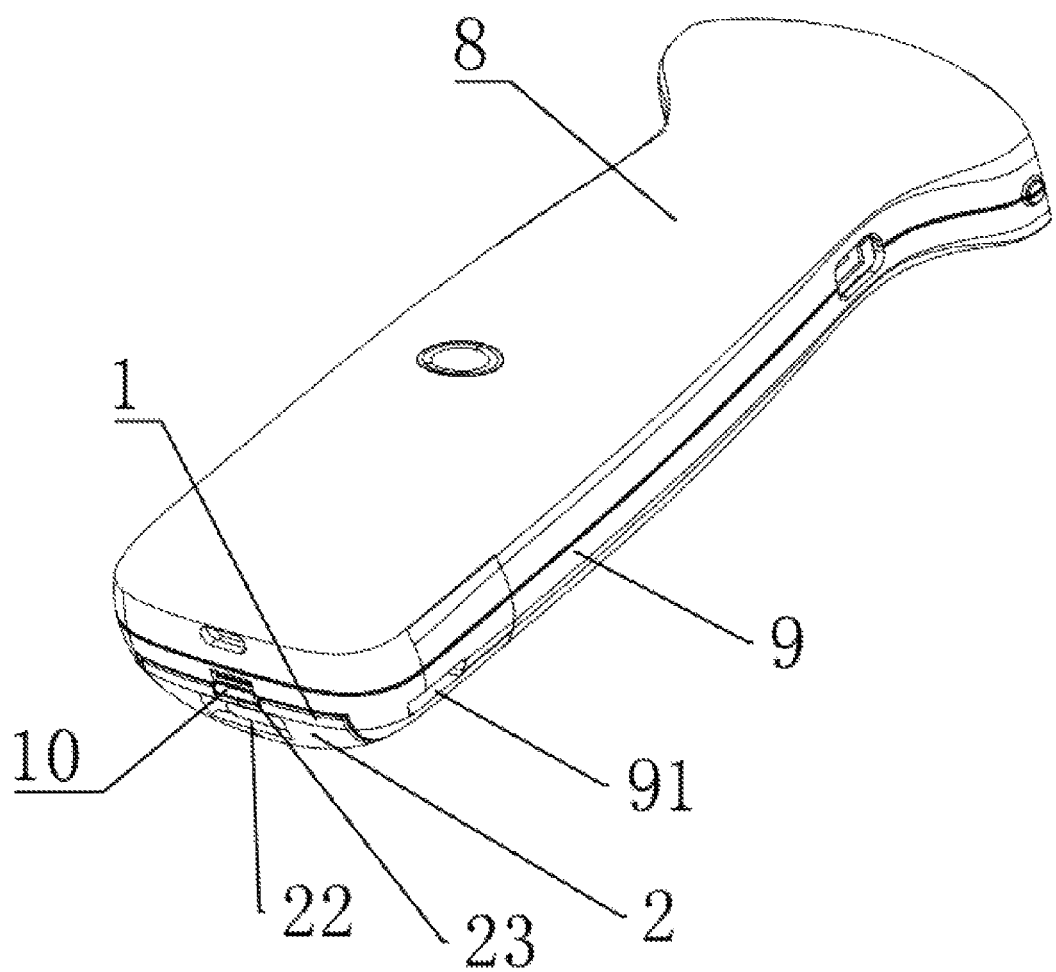
FIG. 3 is a structural diagram of a portable diagnostic ultrasound apparatus disclosed in an embodiment.

The embodiment of the present disclosure discloses a portable diagnostic ultrasound apparatus, as shown in FIG. 3, including: a main body front housing 8, a main body bottom housing 9, and the above-described detachment structure for the portable diagnostic ultrasound apparatus, the detachment structure being detachably connected in the main body bottom housing 9. In the specific implementation, a heat sink is installed in the main body bottom housing 9, and air inlets 91 communicating with the air outlet 22 are formed in a side wall of the main body bottom housing 9. In the specific implementation, the number of the air inlets 91 is set to be two, and the two air inlets 91 are distributed on two opposite sides of the main body bottom housing 9.

It should to be noted that since the detachment structure is detachably connected in the main body bottom housing 9, the convenience of replacing the battery or the fan 4 is satisfied, and the entire apparatus does not need to be returned to the manufacturer for maintenance.

It should also be noted that the detachment structure is waterproof, and the waterproof level can reach IPX7. Users can use alcohol and other disinfectants to disinfect the battery surface without damaging the internal components.

As shown in FIG. 3, the main body bottom housing 9 is rotationally connected with a rotating switch 10 for clamping the bottom housing 2, and the rotating switch 10 is sleeved with a torsion spring. In the specific implementation, the rotating switch 10 is clamped into the undercut 23, thus preventing the detachment structure from slipping off the portable diagnostic ultrasound apparatus.

Figure 4:
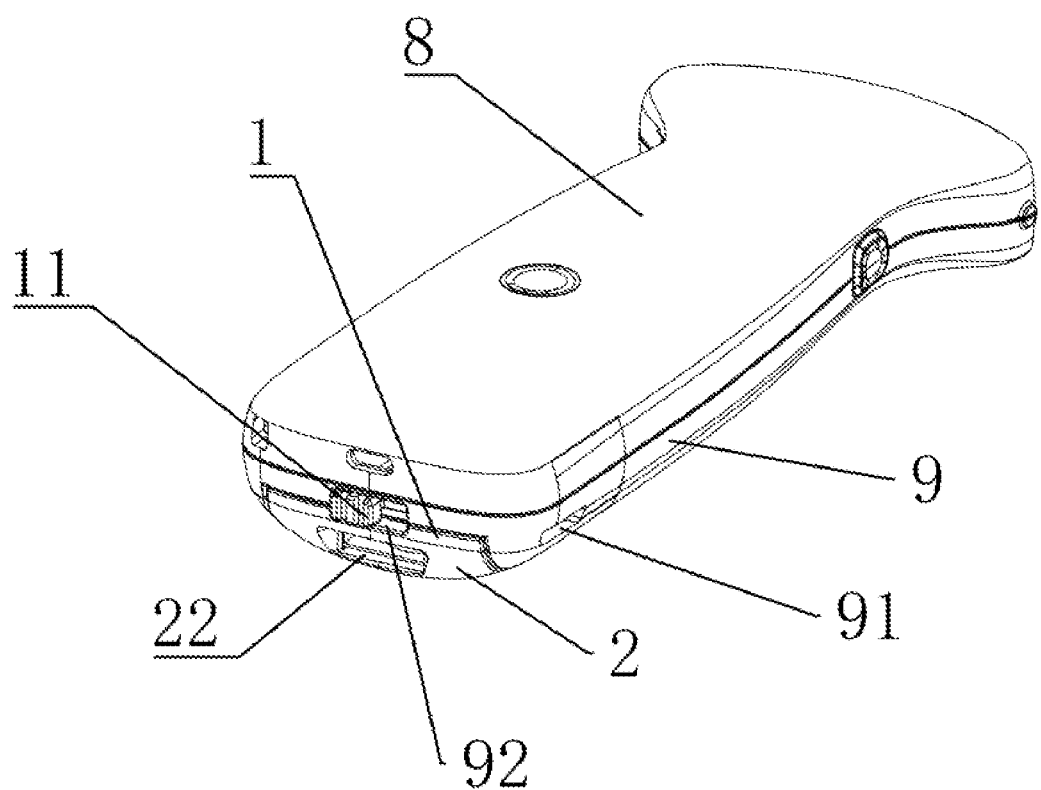
FIG. 4 is a structural diagram of another portable diagnostic ultrasound apparatus disclosed in an embodiment.

As shown in FIG. 4, the main body bottom housing 9 is provided with a toggle switch 11 which is slidingly connected by a pressing spring for pressing the detachment structure, the pressure spring is installed inside the main body bottom housing 9 for pressing the toggle switch 11. In the specific implementation, the detachment structure is provided with a notch for conveniently sliding out of the detachment structure. By pushing the toggle switch 11 and pressing the pressure spring, the toggle switch 11 completely enters the notch, which is convenient for taking out the detachment structure. Moreover, the toggle switch 11 is prevented from moving in the main body bottom housing 9 by the pressing action of the pressure spring, so that the toggle switch 11 can more firmly abut the detachment structure.

Obviously, the above embodiments are only examples for clear explanation, not for limitation of embodiments. For those of ordinary skills in the art, other variations or alterations in different forms can be made on the basis of the above description. It is unnecessary and impossible to enumerate all the embodiments here. The obvious variations or alterations caused by this are still within the protection scope created by the disclosure.

What is claimed is:

1. A portable diagnostic ultrasound apparatus, comprising: a main body front housing, a main body bottom housing, and a detachment structure, the detachment structure being detachably connected within the main body bottom housing; wherein the detachment structure comprising a top cover, a bottom housing, and a rechargeable battery installed between the top cover and the bottom housing, the top cover is detachably connected with the bottom housing, a fan is installed in the bottom housing, the fan is abutted with the top cover, a battery PCB is installed in the bottom housing, the battery PCB is provided with a battery modular contact, the top cover is provided with an opening for the battery modular contact to pass through.

2. The portable diagnostic ultrasound apparatus according to claim 1, wherein the main body bottom housing is rotationally connected with a rotating switch for clamping the bottom housing, and the rotating switch is sleeved with a torsion spring.

3. The portable diagnostic ultrasound apparatus according to claim 1, wherein the main body bottom housing is provided with a toggle switch which is slidingly connected by a pressing spring for pressing the detachment structure, the pressure spring is installed inside the main body bottom housing for pressing the toggle switch.

4. The portable diagnostic ultrasound apparatus according to claim 1, wherein the bottom housing is provided with a slot for facilitating embedded installation of the top cover.

5. The portable diagnostic ultrasound apparatus according to claim 1, the bottom housing is provided with an air outlet.

6. The portable diagnostic ultrasound apparatus according to claim 1, the battery PCB is provided with a charging interface for charging the rechargeable battery.

7. The portable diagnostic ultrasound apparatus according to claim 6, the charging interface is a TYPE-C interface.

8. The portable diagnostic ultrasound apparatus according to claim 1, the bottom housing is provided with an undercut for facilitating clamping of the detachment structure.

9. The portable diagnostic ultrasound apparatus according to claim 1, the circumference of the bottom housing is provided with a groove, and the top cover is provided with protrusions corresponding to the groove, and the groove is filled with waterproof glue therein.

* * * * *